United States Patent
Park et al.

(10) Patent No.: US 8,938,112 B2
(45) Date of Patent: Jan. 20, 2015

(54) METHOD AND APPARATUS FOR CORRECTING POSITRON EMISSION TOMOGRAPHY IMAGE

(71) Applicant: Samsung Electronics Co., Ltd., Suwon-si (KR)

(72) Inventors: Byung-kwan Park, Seoul (KR); Seong-deok Lee, Seongnam-si (KR); Tae-yong Song, Hwaseong-si (KR); Jae-mock Yi, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 16 days.

(21) Appl. No.: 13/739,899

(22) Filed: Jan. 11, 2013

(65) Prior Publication Data

US 2013/0182928 A1 Jul. 18, 2013

(30) Foreign Application Priority Data

Jan. 12, 2012 (KR) ........................ 10-2012-0003856

(51) Int. Cl.
*G06K 9/00* (2006.01)
*G06T 7/00* (2006.01)
*G06T 5/00* (2006.01)
*G06T 5/50* (2006.01)
*A61B 6/00* (2006.01)
*A61B 5/05* (2006.01)

(52) U.S. Cl.
CPC ............... *G06T 7/0012* (2013.01); *G06T 5/003* (2013.01); *G06T 5/50* (2013.01); *G06T 2200/04* (2013.01); *G06T 2207/10081* (2013.01); *G06T 2207/10088* (2013.01); *G06T 2207/10104* (2013.01); *G06T 2207/30004* (2013.01)

USPC .................. 382/131; 378/4; 378/8; 600/410; 600/425

(58) Field of Classification Search
CPC ..................................... G06T 1/00; G06K 1/00
USPC ......... 382/128, 129, 130, 131, 132, 133, 134, 382/190; 378/4, 8, 21–27, 101, 901; 600/407, 410, 411, 425, 427; 128/920, 128/922
See application file for complete search history.

(56) References Cited

U.S. PATENT DOCUMENTS

| 7,580,620 | B2 * | 8/2009 | Raskar et al. .................... 396/55 |
| 7,920,670 | B2 * | 4/2011 | Hugg et al. ......................... 378/4 |
| 2008/0137930 | A1 | 6/2008 | Rosen |

(Continued)

FOREIGN PATENT DOCUMENTS

| JP | 2006-75596 A | 3/2006 |
| JP | 2008-149147 A | 7/2008 |
| KR | 10-2009-0068416 A | 6/2009 |

OTHER PUBLICATIONS

P. Olmos et al., "Design of a modified uniform redundant-array mask for portable gamma cameras," *Applied Optics*, vol. 31, No. 23, Aug. 10, 1992, pp. 4742-4750.

*Primary Examiner* — Abolfazl Tabatabai
(74) *Attorney, Agent, or Firm* — NSIP Law

(57) ABSTRACT

An image correction method includes detecting signals emitted from a tracer introduced into a target; intermittently extracting some of the detected signals according to a code string in which different codes are arranged; generating an image of the target using the extracted signals; and correcting the generated image based on at least one characteristic of the generated image.

18 Claims, 8 Drawing Sheets

(56) References Cited

U.S. PATENT DOCUMENTS

2008/0273785 A1 11/2008 Kesner
2010/0067765 A1 3/2010 Buther et al.
2010/0290683 A1 11/2010 Demeester et al.

* cited by examiner

METHOD AND APPARATUS FOR CORRECTING POSITRON EMISSION TOMOGRAPHY IMAGE

CROSS-REFERENCE TO RELATED APPLICATIONS

This application claims the benefit of Korean Patent Application No. 10-2012-0003856 filed on Jan. 12, 2012, in the Korean Intellectual Property Office, the disclosure of which is incorporated herein by reference in its entirety for all purposes.

BACKGROUND

1. Field

This application relates to methods and apparatuses for correcting a positron emission tomography (PET) image.

2. Description of Related Art

Medical imaging devices that are used to obtain images of internal parts of a body to diagnose patients provide data required to diagnose diseases. Medical imaging methods currently used in hospitals or being developed are mainly classified into an anatomical imaging method and a physiological imaging method. Techniques for capturing high-resolution anatomical images of the body include magnetic resonance imaging (MRI) and computed tomography (CT). These techniques represent accurate positions and shapes of organs of the body by capturing a tomography image of the body or by generating a three-dimensional (3D) image based on a plurality of tomography images. A representative example of a physiological imaging technique is positron emission tomography (PET) for capturing images of internal parts of the body to diagnose a metabolic disorder.

PET is an imaging technology in which a special radioactive tracer for emitting positrons is generated in the form of a metabolic component and is introduced into the body via an intravenous injection or an inhalation method, and two gamma rays at 511 keV emitted in opposite directions when positrons emitted from the tracer combine with electrons are detected by an external device, thereby detecting the position of the tracer and observing a distribution pattern of the tracers and a distribution variation according to time.

In general, in comparison to the total number of actually generated gamma rays, only a very small number of gamma rays reach the detector due to dispersion or attenuation. Thus, a relatively long detection time of several minutes is required to ensure a sufficient amount of detected gamma rays. However, since organs of a healthy person move in relatively short cycles due to breathing or heartbeat, if images of a target are captured for several minutes, motion of the target is reflected in the images, and thus image blur occurs. The above phenomenon in which an image is blurred due to relative motion between an imaging device and a subject is referred to as motion blur, and is a main factor reducing the resolution of a PET image. A deblurring operation for compensating for motion blur is required to correct an image having motion blur. In general, the deblurring operation causes amplification of noise to infinity at certain frequencies.

SUMMARY

In one general aspect, an image correction method includes detecting signals emitted from a tracer introduced into a target; intermittently extracting some of the detected signals according to a code string in which different codes are arranged; generating an image of the target using the extracted signals; and correcting the generated image based on at least one characteristic of the generated image.

The code string may include first codes representing time periods for extracting the detected signals and second codes representing time periods for not extracting the detected signals arranged in a sequence in the code string; and the intermittently extracting may include matching the detected signals to the codes in the code string in a one-to-one correspondence; and extracting detected signals of time periods corresponding to the first codes in the code string from the detected signals.

The generated image may be a positron emission tomography (PET) image; the image correction method may further include obtaining at least one auxiliary image of the target in addition to the PET image; and determining a motion direction of the target as a characteristic of the PET image using the at least one auxiliary image; and the correcting may include correcting the PET image based on the determined motion direction.

The code string may include first codes and second codes irregularly arranged in a sequence in the code string.

The code string may include first codes and second codes arranged in a sequence in the code string according to an input of a user.

The code string may include first codes and second codes arranged in a sequence in the code string; and a ratio of a number of the first codes in the code string to a number of the second codes in the code string may be equal to or greater than a predetermined reference value.

The correcting may include estimating a first filter representing motion blur of the generated image; generating a second filter that is an inverse filter of the first filter using the first filter; and compensating for the motion blur of the generated image using the second filter.

The compensating may include compensating for the motion blur of the generated image by convolving the second filter with the generated image.

The generating of a second filter may include converting the first filter into a frequency domain as part of generating the second filter; and all values obtained by converting the first filter into the frequency domain may be equal to or greater than a predetermined minimum value.

The generating of a second filter may include converting the first filter into a frequency domain as part of generating the second filter; and a difference between a largest value and a smallest value of values obtained by converting the first filter into the frequency domain may be equal to or less than a predetermined reference value.

In another general aspect, a nontransitory computer-readable storage medium stores a computer program for controlling a computer to perform the image correction method described above.

In another general aspect, an image correction apparatus includes a detection unit configured to detect signals emitted from a tracer introduced into a target; an extraction unit configured to intermittently extract some of the detected signals according to a code string in which different codes are arranged; a conversion unit configured to generate an image of the target using the extracted signals; and a correction unit configured to correct the generated image based on at least one characteristic of the generated image.

The code string may include first codes representing time periods for extracting the detected signals and second codes representing time periods for not extracting the detected signals arranged in a sequence in the code string; and the extraction unit may be further configured to match the detected signals to the codes in the code string in a one-to-one correspondence, and extract detected signals of time periods corresponding to the first codes in the code string from the detected signals.

The generated image may be a positron emission tomography (PET) image; the image correction apparatus may further include an auxiliary detection unit configured to obtain at least one auxiliary image of the target in addition to the PET image; and an image analysis unit configured to determine a motion direction of the target as a characteristic of the PET image using the at least one auxiliary image; and the correction unit may be further configured to correct the PET image based on the determined motion direction.

The code string may include first codes and second codes irregularly arranged in a sequence in the code string.

The code may include first codes and second codes arranged in a sequence in the code string; and a ratio of a number of the first codes in the code string to a number of the second codes in the code string may be equal to or greater than a predetermined reference value.

The correction unit may include an estimation unit configured to estimate a first filter representing motion blur of the generated image; and a compensation unit configured to generate a second filter that is an inverse filter of the first filter using the first filter, and compensate for the motion blur of the generated image using the second filter.

The compensation unit may be further configured to compensate for the motion blur of the image by convolving the second filter with the generated image.

The compensation unit may be further configured to convert the first filter into a frequency domain as part of generating the second filter; and all values obtained by converting the first filter into the frequency domain may be equal to or greater than a predetermined minimum value.

The compensation unit may be further configured to convert the first filter into a frequency domain as part of generating the second filter; and a difference between a largest value and a smallest value of values obtained by converting the first filter into the frequency domain may be equal to or less than a predetermined reference value.

Other features and aspects will be apparent from the following detailed description, the drawings, and the claims.

DETAILED DESCRIPTION

Figure 1:
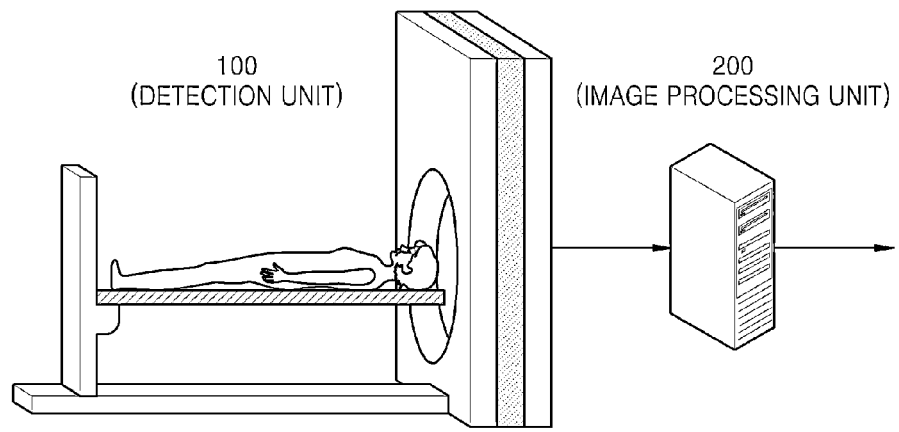
FIG. 1 is a diagram illustrating an example of an image correction apparatus.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

Methods currently used to compensate for motion blur of a positron emission tomography (PET) image mainly include a gating method for adjusting the number of exposures, and an image correction method for compensating for motion blur of an image itself.

In the gating method, when images of a target that moves periodically are captured, only data of a certain time of every cycle is collected from all received data to generate an image. Since the above image is generated by collecting only data of time periods in which the target is located at a certain position and has a certain shape in each cycle, motion blur does not exist, like in a still image. Accordingly, an operation of compensating for motion blur is not required. However, since only some data from all collected data is used, the amount of usable data is reduced, and thus a signal-to-noise ratio (SNR) is decreased. In order to achieve the same SNR, signals have to be detected for a long time to obtain a large amount of data, and thus a long detection time is required.

In the image correction method, point spread function (PSF) estimation and frequency domain analysis are performed. In greater detail, an image having motion blur may be regarded as a result of convolving a still image with a two-dimensional (2D) filter. Accordingly, a filter may be estimated by analyzing the image having the motion blur, and an inverse filter of the estimated filter may be convolved with the image having the motion blur to obtain a still image. Since all detected and collected data are used in this method, a relatively high SNR may be achieved. However, due to a zero-crossing phenomenon that occurs when the inverse filter is applied, noise at certain frequencies is amplified to infinity, and thus the performance of this method is not perfect.

The zero-crossing phenomenon refers to a phenomenon in which noise is greatly amplified in some parts of an image when an inverse filter is convolved with the image because the inverse filter diverges to infinity at certain frequencies.

In greater detail, if an image is generated using data collected by a continuous exposure instead of gating, a filter estimated using the generated image has a box shape, and the box-shaped filter has a form of a sinc function when it is converted into the frequency domain. A sinc function has a value of 0 at certain frequencies referred to as zero-crossing frequencies. Accordingly, an inverse filter of the box-shaped filter diverges to infinity at the zero-crossing frequencies. If the inverse filter is convolved with an image, noise in the image is amplified to infinity at the zero-crossing frequencies.

Hereinafter, methods and apparatuses for correcting an image by compensating for motion blur to achieve a certain level of an SNR and to minimize noise in the image amplified due to the zero-crossing phenomenon will be described in detail.

FIG. 1 is a diagram illustrating an example of an image correction apparatus. Referring to FIG. 1, the image correction apparatus includes a detection unit 100 and an image processing unit 200. The image correction apparatus detects signals emitted from a tracer introduced into a target and processes an image generated using the detected signals.

The detection unit 100 detects signals emitted from a tracer introduced into a target and transmits data of the detected signals to the image processing unit 200. For example, the detection unit 100 detects gamma rays emitted from a target of which a positron emission tomography (PET) image is to be captured, and transmits line-of-response (LOR) data of the detected gamma rays to the image processing unit 200.

LOR data is data representing a linear emission path of a pair of gamma rays emitted from the target at an angle of 180° relative to each other. The LOR data includes data such as an incident angle of a gamma ray on the detector, a displacement from a position where the gamma ray is emitted to the detector, a time when the gamma ray is detected, and an energy of the gamma ray.

The image processing unit 200 receives the data from the detection unit 100, extracts some of the received data, generates an image by converting the extracted data into image data, and corrects the generated image by compensating for motion blur of the image.

Methods of compensating for motion blur of a PET image include a gating method and an image correction method. In the gating method, only some data is extracted and converted to generate an image. In the image correction method, all data is converted to generate an image and the generated image is corrected by compensating for motion blur of the image. The image processing unit 200 may use these two methods. Detailed descriptions thereof will be provided below with reference to FIG. 2.

Figure 2:
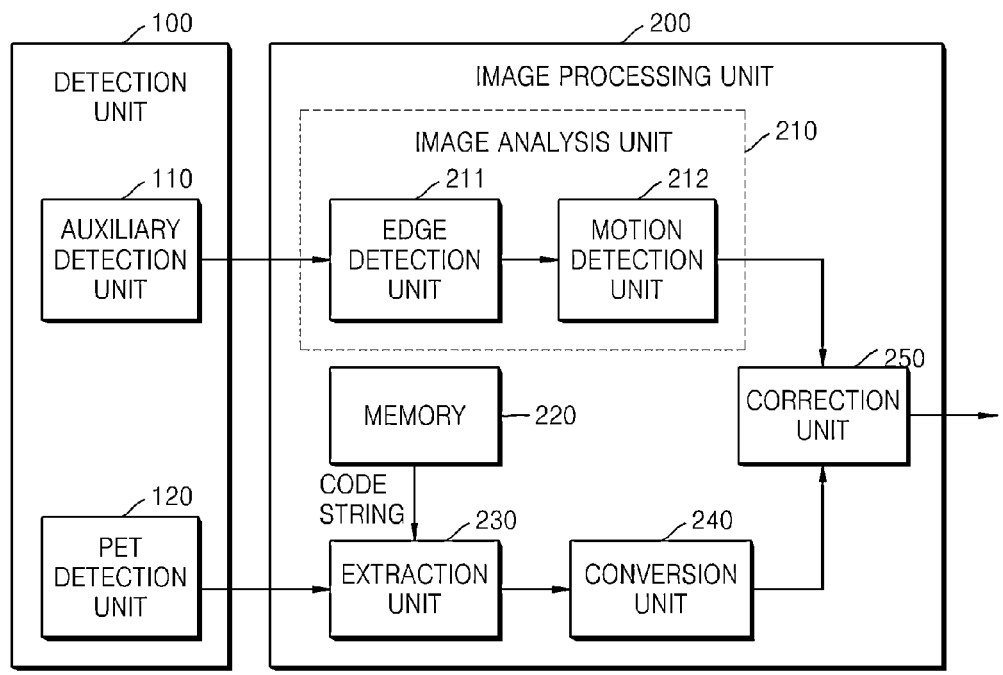
FIG. 2 is a block diagram of an example of the image correction apparatus illustrated in FIG. 1.

FIG. 2 is a block diagram of the image correction apparatus illustrated in FIG. 1. Referring to FIG. 2, the detection unit 100 of the image correction apparatus includes an auxiliary detection unit 110 and a PET detection unit 120, and the image processing unit 200 of the image correction apparatus includes an image analysis unit 210, a memory 220, an extraction unit 230, a conversion unit 240, and a correction unit 250. The image analysis unit 210 includes an edge detection unit 211 and a motion detection unit 212.

The image correction apparatus detects signals emitted from a tracer introduced into a target, intermittently extracts some of the detected signals according to a code string in which different values are arranged in a sequence, generates an image of the target using the extracted signals, obtains one or more auxiliary images of the target, obtains at least one characteristic of the generated image from the one or more auxiliary images, and corrects the generated image based on the at least one characteristic of the generated image.

The memory 220 is a type of storage device. The memory 220 stores a code string for determining LOR data to be extracted by the extraction unit 230 from the LOR data received from the detection unit 100.

For example, the code string stored in the memory 220 may be a code string in which a first code indicating that LOR data is to be extracted from the LOR data received from the detection unit 100 and a second code indicating that LOR data is not to be extracted from the LOR data are arranged in a sequence randomly or based on a certain rule. For example, the first code in the code string may have a value of 0 and the second code in the code string may have a value of 1. In such an example, the code string is a binary sequence of values of 0 and 1. The code string may be previously input into the memory 220 by a user, may be generated due to calculation by a computer and stored in the memory 220, or may be input in real time. A method of generating a code string is not limited to these methods.

The PET detection unit 120 detects signals emitted from a tracer introduced into a target. The target may be a living thing such as an animal or a person. If the target is a person, a user generates a special radioactive tracer for emitting positrons in the form of a metabolic component, and introduces the tracer into the body via an intravenous injection or inhalation method. The introduced tracer emits positrons, and the emitted positrons combine with electrons, causing a pair of gamma rays at 511 keV to be emitted in opposite directions. The detection unit 100 detects the pair of gamma rays. The detection unit 100 collects data of the detected pair of gamma rays in the form of LOR data and transmits the collected data to the image processing unit 200.

Positrons are a type of radiation, and are emitted from radioactive isotopes such as C-11, N-13, O-15, and F-18. Since these elements are some of the elements that make up a living body, special radioactive tracers for a living body are generated using these elements. The most commonly used tracer includes a glucose analog such as fluorine-18 fluorodeoxyglucose (F-18 FDG). When this tracer is injected, the tracer is concentrated in a body part where glucose metabolism occurs actively, e.g., cancer cells.

The extraction unit 230 intermittently extracts some of the signals detected by the PET detection unit 120 according to a code string in which different values are arranged in a sequence. The signals may be LOR data and the code string may be the code string stored in the memory 220. The PET detection unit 120 detects gamma rays at certain intervals and thus the LOR data may be arranged in a sequence at certain intervals in time order. The LOR data may include detection time data. For example, the obtained code string may be a binary sequence of values of 0 and 1 and some of the LOR data may be extracted according to the code string. A method of extracting LOR data according to a code string will be described in detail below with reference to FIG. 5.

In this example, a total number of codes in the code string is equal to or greater than a total number of the LOR data, and thus all of the LOR data may correspond one-to-one to codes in the code string. That is, each of the LOR data may correspond one-to-one to a respective code in the code string. If the code string is a binary code string, the binary code string may be generated using a pseudo-random algorithm or a modified uniformly redundant array (MURA) algorithm, or may be determined by a user.

The pseudo-random algorithm is an algorithm for generating 0 or 1 as an output value when a certain value is input. Since an unpredictable value such as a current time in a computer system is used as an input value, the output value is also unpredictable, and a user perceives the output value as a randomly obtained value. Accordingly, it may be regarded that values of 0 and 1 are randomly arranged in a code string generated using a pseudo-random algorithm.

MURA codes have been developed to discontinuously open a shutter of a camera in order to effectively eliminate noise, and may be represented in the form of binary codes. MURA codes are represented as a flat line in a graph when they are converted into the frequency domain. Due to the above characteristics, the zero-crossing phenomenon that occurs when an image is deblurred may be reduced.

MURA codes are described in detail in various documents. For example, one of ordinary skill in the art would understand MURA codes by referring to P. Olmos et al., "Design of a modified uniform redundant-array mask for portable gamma cameras," *Applied Optics*, Vol. 31, No. 23, Aug. 10, 1992, pp. 4742-4750.

MURA codes are described in detail in various documents. For example, one of ordinary skill in the art would understand MURA codes by referring to P. Olmos et al., "Design of a modified uniform redundant-array mask for portable gamma cameras," *Applied Optics*, Vol. 31, No. 23, Aug. 10, 1992, pp. 4742-4750.

A method of configuring a code string is not limited to the above-mentioned examples, and various methods may be used. Since the effects of the zero-crossing phenomenon may be reduced or eliminated by appropriately configuring a code string, the configuration of a code string may be a factor for determining the performance of image correction. Reduction or elimination of the effects of the zero-crossing phenomenon will be described below in detail with reference to FIGS. 6 through 8.

A ratio of a number of the LOR data extracted by the extraction unit 230 to a number of all of the LOR data obtained by the PET detection unit 120 influences an SNR. For example, the number of LOR data extracted by the extraction unit 230 according to the code string and then transmitted to the conversion unit 240 is less than the number of all of the LOR data obtained by the PET detection unit 120, and due to the reduced amount of data, the SNR is relatively decreased. Since the conversion unit 240 generates an image by converting the extracted LOR data, the number of extracted LOR data directly relates to the SNR of the generated image.

For example, for a given number of LOR data transmitted from the PET detection unit 120 to the extraction unit 230, if the number of LOR data extracted by the extraction unit 230 is small, the number of LOR data used for image conversion is reduced, such that the SNR is decreased and image quality is reduced. Accordingly, when a code string is configured, a user may determine a ratio of data to be extracted in order to adjust the SNR.

If the code string is a binary code string, a user may determine a ratio of a total number of values of 1 to a total number of values of 0 in the entire code string. Accordingly, a ratio of data to be extracted may be determined by the user, and certain levels of sensitivity and SNR may be ensured. A higher ratio of data to be extracted will result in a higher sensitivity and a higher SNR, and a lower ratio of data to be extracted will result in a lower sensitivity and a lower SNR.

If the code string is a binary code string generated according to a pseudo-random algorithm, due to characteristics of the pseudo-random algorithm, one of ordinary skill in the art would understand that if the length of the code string is sufficiently long, a ratio of a number of values of 1 to a number of values of 0 in the entire code string will be close to 50%. Since the extraction unit 230 extracts the LOR data according to the number of values of 1 in the code string, a ratio of the number of LOR data extracted by the extraction unit 230 and transmitted to the conversion unit 240 to the number of all of the LOR data received from the PET detection unit 120 will also be close to 50%, enabling a user to ensure a desired sensitivity and a desired SNR.

The conversion unit 240 generates an image of the target using the extracted signals. For example, the conversion unit 240 receives the LOR data extracted by the extraction unit 230, calculates the position of the tracer using the received LOR data, and generates the image of the target by displaying the position of the tracer on an anatomical image of the target. An example of estimating the position of a tracer using the LOR data will be described below with reference to FIG. 4.

According to another example, in order to obtain a higher-resolution tomography image of a target, an anatomical imaging apparatus such as a computed tomography (CT) apparatus or a magnetic resonance imaging (MRI) apparatus may be used. Since a PET apparatus is generally combined with an anatomical imaging apparatus such as a CT or MRI apparatus, a high-resolution tomography image of a target may be obtained using a CT or MRI apparatus.

The auxiliary detection unit 110 obtains one or more auxiliary images of the target that are combined with a low-resolution PET image to supplement the PET image. For example, the auxiliary detection unit 110 may be an MRI or CT apparatus. In comparison to a PET apparatus, an MRI or CT apparatus has a shorter detection time, and thus provides a higher-resolution tomography image. Also, an MRI or CT apparatus may capture a plurality of images at short intervals and may compare the captured images. Accordingly, the auxiliary detection unit 110 may transmit a plurality of anatomical images of the target captured at certain intervals to the image analysis unit 210, and the image analysis unit 210 may compare the anatomical images to recognize a variation pattern of the target over time.

The edge detection unit 211 of the image analysis unit 210 receives the anatomical images of the target from the auxiliary detection unit 110 and recognizes shapes of organs in the received anatomical images. For example, the edge detection unit 211 detects a line element representing a boundary of an object in an image, and extracts a certain object, and measures an area, position, and size of the object. Also, the edge detection unit 211 may detect a line element of the target in each of the anatomical images obtained at certain intervals in the above-described manner. The motion detection unit 212 of the image analysis unit 210 detects a motion of the line element by comparing the line elements recognized by the edge detection unit 211 in the anatomical images obtained at certain intervals, and thus may determine, for example, directions and patterns in which the organs of the target move.

The correction unit 250 corrects the image generated by the conversion unit 240 based on at least one characteristic of the image. For example, the correction unit 250 receives the image converted by the conversion unit 240, receives information regarding motion of the target from the image analysis unit 210 as a characteristic of the image, and corrects the image received from the conversion unit 240 based on the information regarding motion of the target received from the image analysis unit 210.

A PET image of the body of a person, for example, the image generated by the conversion unit 240, may include motion blur of organs of the body due to regular motion of the body, e.g., heartbeat or breathing. Also, although only some LOR data is extracted by the extraction unit 230, since the extracted LOR data is obtained not by extracting only data corresponding to a certain position in each cycle, but by extracting the LOR data according to the code string regardless of the cycles, motion blur may still exist. In order to compensate for such motion blur, the correction unit 250 applies the principle of image convolution.

The principle of image convolution may be applied by inversely using the principle of generating an image having motion blur by convolving a point spread function (PSF) filter representing a degree of spread of a point in an image with a still image.

For example, the correction unit 250 may estimate a PSF filter representing motion blur of the PET image received from the conversion unit 240 based on the information regarding the motion of the target received from the image analysis unit 210, generate an inverse filter of the estimated PSF filter, and convolve the inverse filter with the PET image received from the conversion unit 240, thereby generating a still PET image in which motion blur of the image is compensated.

The technique of estimating a PSF filter using an image having motion blur is referred to as PSF estimation. As one example of the PSF estimation, the correction unit 250 may detect a linear element of the target in the PET image received from the conversion unit 240, analyze an outline of the detected line element, and compare the analyzed outline to a line element of the target in a stationary state and having a form of a step function, thereby estimating a two-dimensional (2D) PSF filter from the PET image received from the conversion unit 250.

However, since a PET image of a target has a low resolution, it may be difficult to accurately estimate a PSF filter from the PET image received from the conversion unit 240. Accordingly, as another example of the PSF estimation, the correction unit 250 may estimate a more accurate PSF filter based on the information regarding the motion of the target received from the image analysis unit 210.

Although not shown in FIG. 2, a display device for outputting the ultimately generated image may also be provided.

Figure 3:
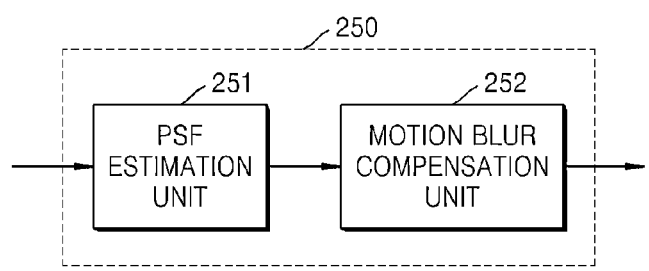
FIG. 3 is a block diagram of an example of a correction unit illustrated in FIG. 2.

FIG. 3 is a block diagram of an example of the correction unit 250 illustrated in FIG. 2. Referring to FIG. 3, the correction unit 250 includes a PSF estimation unit 251 and a motion blur compensation unit 252. The PSF estimation unit 251 estimates a PSF filter representing motion blur of the image received from the conversion unit 240, and the motion blur compensation unit 252 compensates for motion blur of the image using the PSF filter estimated by the PSF estimation unit 251 according to the following Equations 1 and 2.

$$I(x,y)=S(x,y)*F(x,y) \quad (1)$$

$$S(x,y)=I(x,y)*F^{-1}(x,y) \quad (2)$$

Equation 1 is an image convolution equation using a PSF filter. Equation 2 is an image deconvolution equation obtained by applying an inverse filter of the PSF filter to Equation 1. In Equations 1 and 2, I(x,y) denotes the image having motion blur received from the conversion unit 250, S(x,y) denotes a still image in which there is no motion blur, F(x,y) represents the PSF filter, $F^{-1}(x,y)$ denotes the inverse filter of the PSF filter, and x and y denote coordinates on horizontal and vertical axes of a 2D image.

The PSF estimation unit 251 estimates a PSF filter (F(x,y)) using the image (I(x,y)) having motion blur received from the conversion unit 240, and the motion blur compensation unit 252 calculates an inverse filter ($F^{-1}(x,y)$) of the estimated PSF filter (F(x,y)), and applies the inverse filter ($F^{-1}(x,y)$) to the image (I(x,y)) having motion blur according to Equation 2, thereby generating the still image (S(x,y)) by convolving the inverse filter ($F^{-1}(x,y)$) with the image (I(x,y)) having motion blur.

Figure 4:
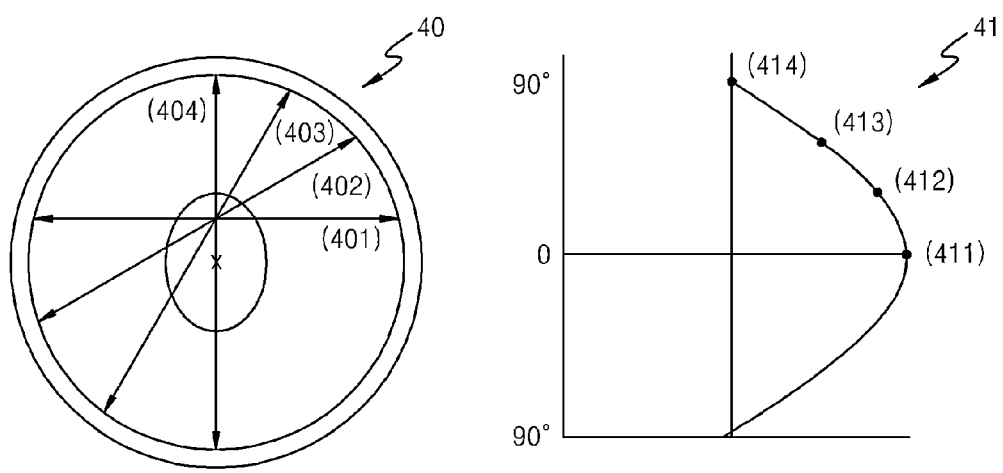
FIG. 4 is a diagram illustrating an example of converting line-of-response (LOR) data into image data performed by a conversion unit illustrated in FIG. 2.

FIG. 4 is a diagram illustrating an example of an operation of converting LOR data into image data performed by the conversion unit 240 illustrated in FIG. 2. The LOR data includes an angle at which a pair of gamma rays are emitted and a displacement from a position where the gamma rays are emitted to a detector. The conversion unit 240 calculates the position where the gamma rays are emitted using the LOR data, and displays the calculated position on a tomography image of a target. In this manner, the conversion unit 240 converts all of the LOR data extracted by the extraction unit 230 into position data of the tracer and displays all of the position data on the tomography image of the target.

Referring to FIG. 4, a graph 41 shows angle data and displacement data included in four LOR data as coordinates, and a FIG. 40 shows positions of a tracer that are calculated using the graph 41. In this case, coordinates 411, 412, 413, and 414 of the graph 41 respectively correspond to straight lines 401, 402, 403, and 404 of the FIG. 40.

Figure 5:
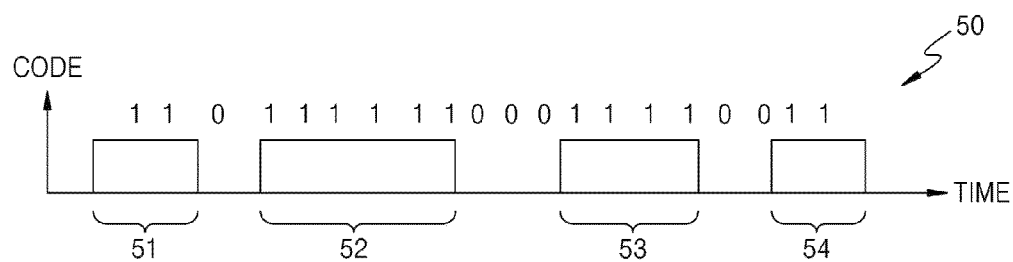
FIG. 5 is a diagram illustrating an example of extracting LOR data of certain time periods according to a code string performed by an extraction unit illustrated in FIG. 2.

FIG. 5 is a diagram illustrating an example of extracting LOR data of certain time periods according to a code string performed by the extraction unit 230 illustrated in FIG. 2. Referring to FIG. 5, a graph 50 shows that codes in the code string obtained by the extraction unit 230 from the memory 220 correspond one-to-one to LOR data arranged in a sequence in time order. The extraction unit 230 extracts LOR data corresponding to a code having a value of 1 from all of the LOR data, discards LOR data corresponding to a code having a value of 0 from all of the LOR data, and transmits the extracted LOR data to the conversion unit 240. In the graph 50, only the LOR data corresponding to time periods 51, 52, 53, and 54 are extracted by the extraction unit 230. The other LOR data not corresponding to the time periods 51, 52, 53, and 54 are discarded by the extraction unit 230

However, the above method of extracting LOR data according to a code string is merely an example, and one of ordinary skill in the art would understand that other methods may also be used to extract LOR data according to code data.

Table 1 illustrates an example of another method of extracting LOR data according to a code string performed by the extraction unit 230.

TABLE 1

| Time | LOR (Angle, Displacement) | Code |
|---|---|---|
| 1* | (20, 0.5) | 1 |
| 2* | (15, 1.5) | 1 |
| 3 | (10, 3.0) | 0 |
| 4* | (15, 1.5) | 1 |
| 5* | (10, 1.0) | 1 |
| 6* | (20, 2.0) | 1 |
| 7 | (20, 2.5) | 0 |
| 8 | (15, 2.0) | 0 |
| 9 | (10, 1.0) | 0 |
| 10* | (5, 1.5) | 1 |
| 11 | (5, 0.5) | 0 |
| 12* | (10, 3.0) | 1 |

Referring to Table 1, * denotes LOR data corresponding to a first code of a code string that is extracted by the extraction unit 230 from all of the LOR data received from the detection unit 120. As described above, the detection unit 120 may detect LOR data at certain intervals and the extraction unit 230 may detect desired data by extracting some of the LOR data arranged in a sequence in time order.

Figure 6:
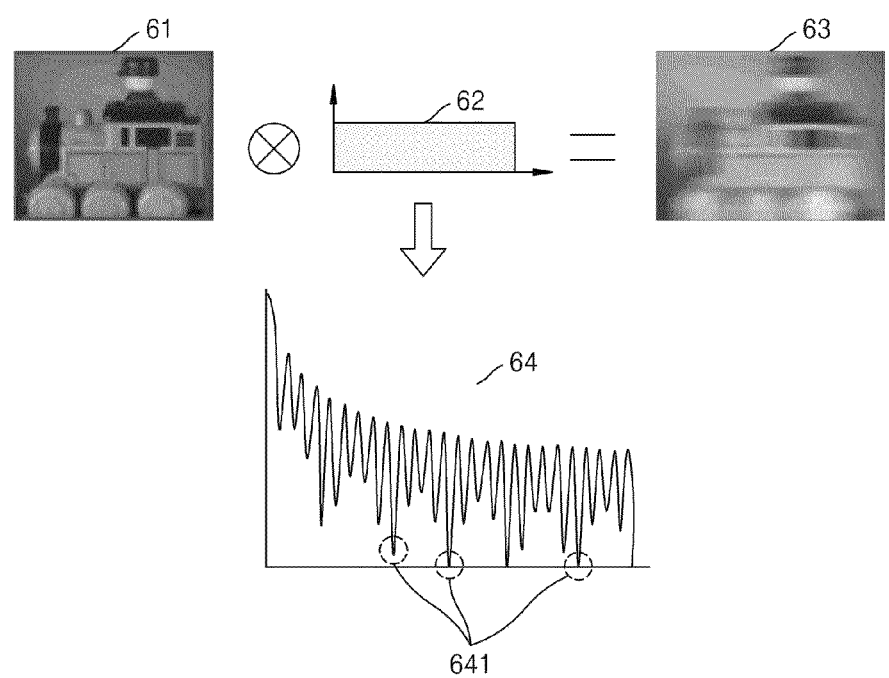
FIG. 6 is a diagram illustrating an example of generating motion blur by convolving a point spread function (PSF) filter with a still image.

FIG. 6 is a diagram showing an example of generating motion blur by convolving a PSF filter 62 with a still image 61. Referring to FIG. 6, as a result of convolving the still image 61 with the PSF filter 62, an image 63 having motion blur is generated. In FIG. 6, the PSF filter 62 is a box-shaped filter that corresponds to a continuous exposure. In order to inversely obtain the still image 61 from the image 63 having motion blur according to Equation 2 discussed above, an inverse filter of the PSF filter 62 is generated.

In order to generate the inverse filter, the PSF filter 62 is converted into the frequency domain. A graph 64 obtained by converting the PSF filter 62 into the frequency domain has a form of a sinc function. The sinc function has a value of 0 at certain frequencies referred to as zero-crossing frequencies 641. The inverse filter has a reciprocal shape of the graph 64 in the frequency domain, and thus has an infinite value at the zero-crossing frequencies 641.

The correction unit 250 illustrated in FIG. 2 generates a still image by convolving the above-described inverse filter with an image having motion blur. In the still image generated by convolving the inverse filter with the image having motion blur, noise is amplified at the zero-crossing frequencies 641, which is referred to as the zero-crossing phenomenon.

Figure 7:
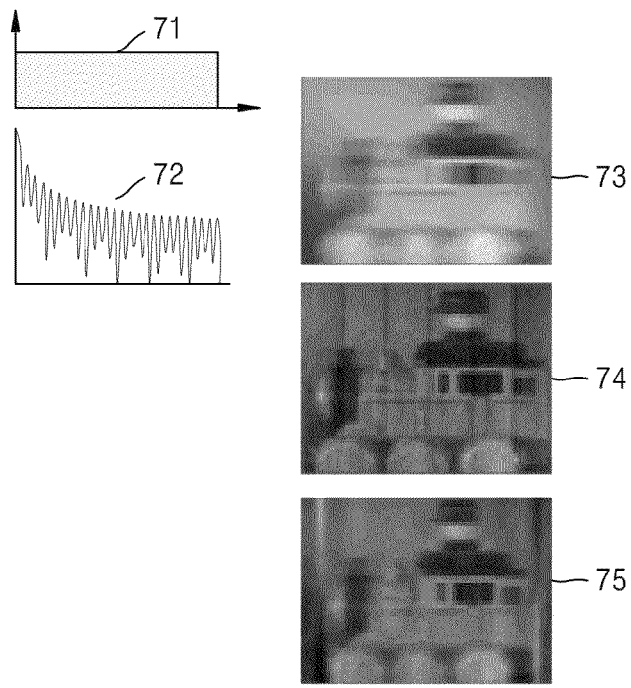
FIG. 7 is a diagram illustrating an example of deblurring an image having motion blur.

FIG. 7 is a diagram illustrating an example of deblurring an image 73 having motion blur. FIG. 7 shows an example of an image captured by continuously exposing a camera, which corresponds to generating an image using all of the LOR data generated by a PET apparatus.

Referring to FIG. 7, a PSF filter 71 estimated using the image 73 having motion blur is converted into the frequency domain, an inverse filter is generated using a graph 72 obtained by converting the PSF filter 71 into the frequency domain, and a still image 74 is generated by convolving the generated inverse filter with the image 73 having motion blur. The graph 72 in the frequency domain has zero-crossing frequencies, so in the generated still image 74, noise is amplified at the zero-crossing frequencies, producing vertical lines in the generated still image 74. The noise in the still image 74 can be seen when the generated still image 74 is compared to an image 75 captured in a stationary state.

Figure 8:
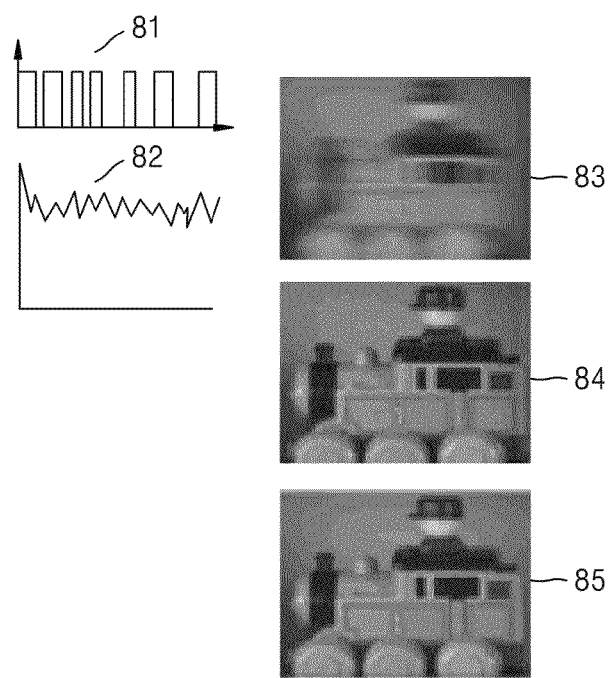
FIG. 8 is a diagram illustrating another example of deblurring an image having motion blur.

FIG. 8 is a diagram illustrating another example of deblurring an image 83 having motion blur. FIG. 8 shows an example of an image captured by discontinuously exposing a camera, which corresponds to generating an image not by using all of the LOR data of a PET apparatus, but by extracting some of the LOR data according to a predetermined code string.

Referring to FIG. 8, a PSF filter 81 estimated using the image 83 having motion blur is converted into the frequency domain, an inverse filter is generated using a graph 82 obtained by converting the PSF filter 81 into the frequency domain, and a still image 84 is generated by convolving the generated inverse filter with the image 83 having motion blur. In this case, the graph 82 in the frequency domain does not have zero-crossing frequencies, so in the generated still image 84, noise is not amplified at such zero-crossing frequencies. No significant difference can be seen when the generated still image 84 is compared to an image 85 captured in a stationary state.

That is, if an image is generated not by using all data, but by extracting only data of predetermined times according to a predetermined code string, the effects of the zero-crossing phenomenon may be reduced or eliminated.

Accordingly, when a code string used in the examples disclosed herein is generated, it should be taken into consideration that values of a frequency domain function of a PSF filter should not be 0 in order to prevent amplification of noise at zero-crossing frequencies of the frequency domain function of the PSF filter. Accordingly, the code string used in the examples disclosed herein may be generated so that the values of the frequency domain function of the PSF filter are equal to or greater than a predetermined minimum value.

Also, when the code string used in the examples disclosed herein is generated, it should be taken into consideration that the values of the frequency domain function of the PSF filter should have a small variation range in order to evenly correct an image over an entire frequency band. Accordingly, the code string used in the examples disclosed herein may be generated so that the values of the frequency domain function of the PSF filter are limited to a certain range, that is, so a difference between a largest value and a smallest value of the values of the frequency domain function of the PSF filter is equal to or less than a predetermined reference value.

Figure 9:
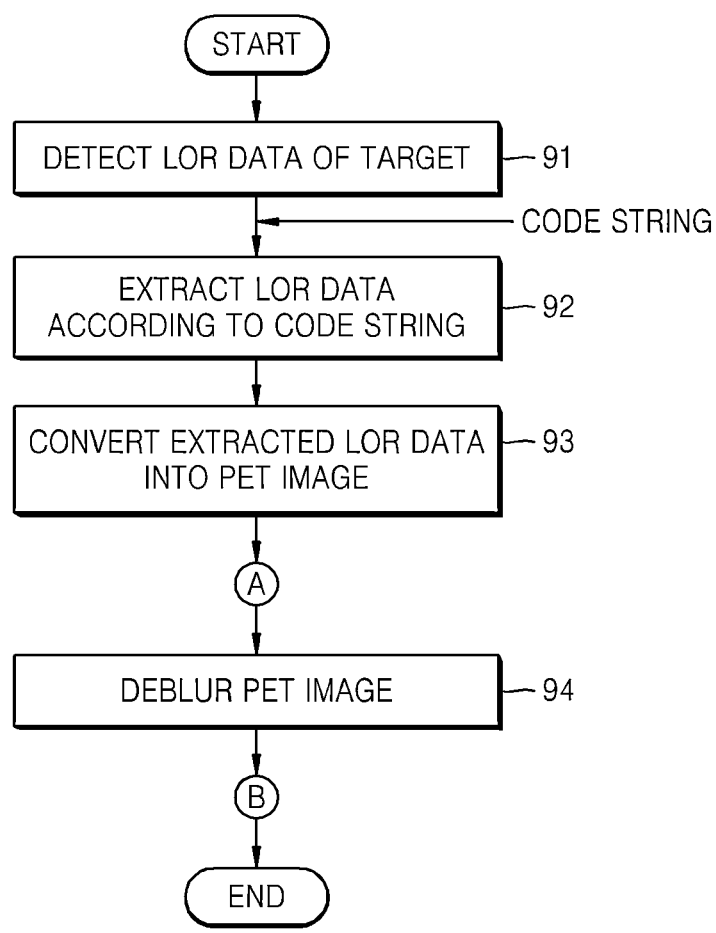
FIG. 9 is a flowchart illustrating an example of an image correction method.

FIG. 9 is a flowchart illustrating an example of an image correction method. As illustrated in FIG. 9, the image correction method includes detecting LOR data of a target (operation 91), extracting LOR data according to a code string including values of 0 and 1 arranged in a sequence (operation 92), converting the extracted LOR data into a PET image (operation 93), and deblurring the PET image (operation 94).

In operation 91, the PET detection unit 120 detects LOR data of gamma rays emitted from the target. In operation 92, the extraction unit 230 extracts only LOR data of desired time periods according to the code string. In operation 93, the conversion unit 240 estimates the position of a tracer using the extracted LOR data and generates a PET image by indicating the position of the tracer in image data. In operation 94, the correction unit 250 compensates for motion blur by deblurring the PET image.

Figure 10:
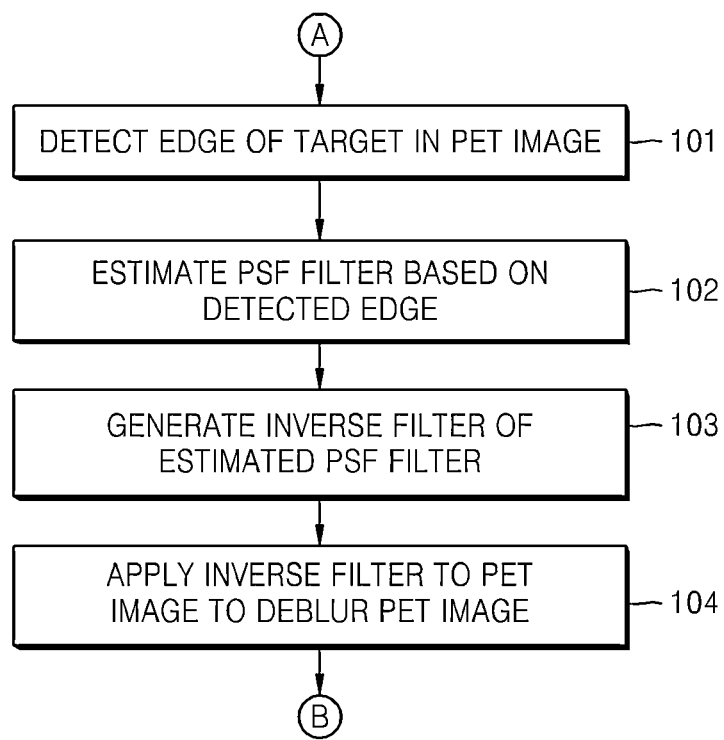
FIG. 10 is a detailed flowchart illustrating an example of a deblurring operation of the image correction method illustrated in FIG. 9.

FIG. 10 is a detailed flowchart illustrating an example of the deblurring operation 94 of the image correction method illustrated in FIG. 9. As illustrated in FIG. 10, the deblurring operation includes detecting an edge of a target in the PET image (operation 101), estimating a PSF filter based on the detected edge (operation 102), generating an inverse filter of the estimated PSF filter (operation 103), and applying the inverse filter to the PET image to deblur the PET image (operation 104).

In operation 101, the PSF estimation unit 251 detects an edge of a target in the PET image received from the conversion unit 250. In operation 102, the PSF estimation unit 251 estimates a PSF filter representing motion blur of the PET image received from the conversion unit 240 based on a comparison between the detected edge of the target and the edge of the target in a stationary state. In operation 103, the motion blur compensation unit 252 generates an inverse filter of the estimated PSF filter. In operation 104, the motion blur compensation unit 252 applies the inverse filter to the PET image received from the conversion unit 240, thereby convolving the inverse filter with the PET image received from the conversion unit 240 to generate a still PET image in which the motion blur is compensated.

Figure 11:
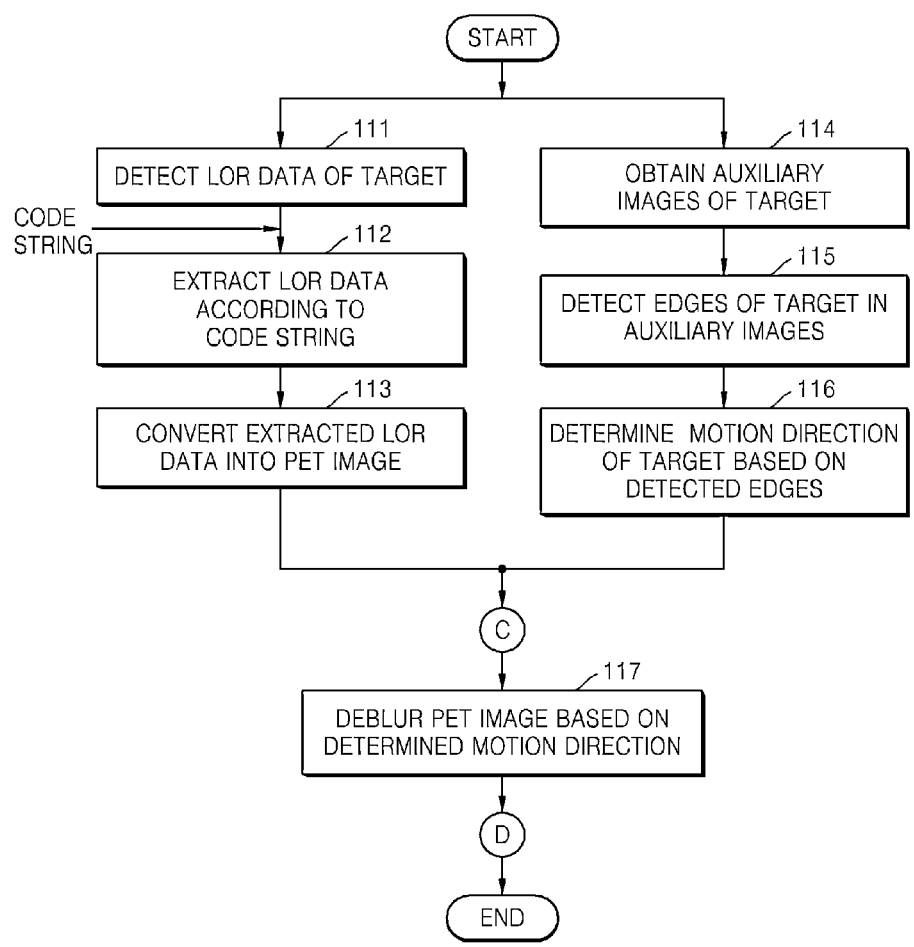
FIG. 11 is a flowchart illustrating another example of an image correction method.

FIG. 11 is a flowchart illustrating another example of an image correction method. Referring to FIG. 11, the image correction method includes detecting LOR data of a target (operation 111), extracting LOR data according to a code string including values of 0 and 1 arranged in a sequence (operation 112), converting the extracted LOR data into PET image (operation 113), obtaining auxiliary images representing anatomical information of the target (operation 114), detecting edges of the target in the obtained auxiliary images (operation 115), determining a motion direction of the target by analyzing the detected edges (operation 116), and deblurring motion blur of the PET image based on the determined motion direction (operation 117).

In operation 114, the auxiliary detection unit 110 obtains auxiliary images representing anatomical information of the target at predetermined intervals using an MRI or CT apparatus combined with a PET apparatus to supplement a low-resolution PET image. Since the MRI or CT apparatus is capable of capturing an image within a very short time in comparison to a PET apparatus, motion blur does not occur in the auxiliary images, so a plurality of clear images may be captured at predetermined intervals by the MRI or CT apparatus and may be compared to each other according to time.

In operation 115, the edge detection unit 211 detects a line element in the auxiliary images representing a boundary of an object, extracts a certain object, and measures an area, position, and size of the object in each of the auxiliary images obtained at predetermined intervals.

In operation 116, the motion detection unit 212 determines a motion direction of the target by comparing the area, position, and size of the target measured by the edge detection unit 211 according to time.

In operation 117, in order to compensate for motion blur of the PET image received from the conversion unit 240, the correction unit 250 deblurs the generated image based on the motion direction determined by the motion detection unit 212.

Figure 12:
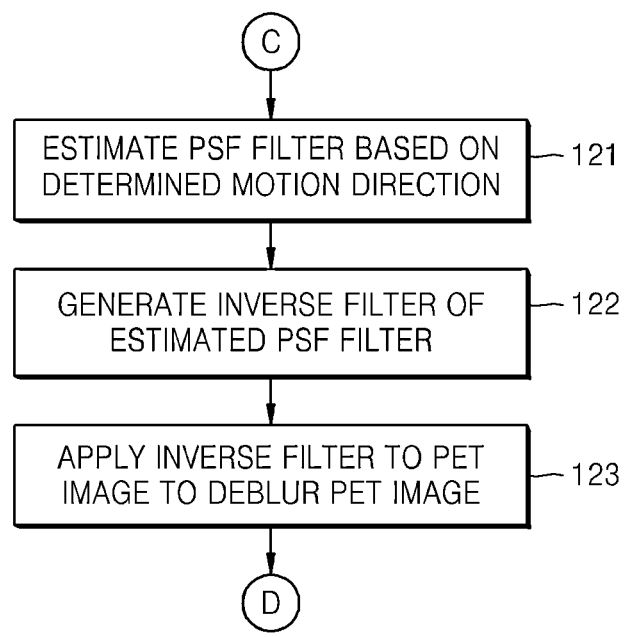
FIG. 12 is a detailed flowchart illustrating an example of a deblurring operation of the image correction method illustrated in FIG. 11.

FIG. 12 is a detailed flowchart illustrating an example of the deblurring operation 117 of the image correction method illustrated in FIG. 11. As illustrated in FIG. 12, the deblurring operation includes estimating a PSF filter based on the determined motion direction (operation 121), generating an inverse filter of the estimated PSF filter (operation 122), and applying the inverse filter to the PET image to deblur the PET image (operation 123).

In operation 121, the PSF estimation unit 251 estimates a PSF filter representing motion blur of the PET image received from the conversion unit 240 based on the determined motion direction received from the motion detection unit 212. In operation 122, the motion blur compensation unit 252 generates an inverse filter of the estimated PSF filter. In operation 123, the motion blur compensation unit 252 applies the inverse filter to the PET image received from the conversion unit 240, thereby convolving the inverse filter with the PET image received from the conversion unit 240 to generate a still PET image in which the motion blur is compensated.

According to the disclosed herein, in a method of correcting an image having motion blur, motion blur may be eliminated and appropriate levels of sensitivity and SNR may be achieved. In a conventional method, when PET images of a target that moves periodically are captured, a method of detecting only signals emitted at a certain time of every cycle has been used to eliminate motion blur. Since the target is at the same position at a certain time of every cycle, motion blur itself is not generated. However, since the number of detected signals is small in comparison to a total number of detectable signals for the entire detecting time, an SNR is relatively decreased. On the other hand, in the above examples, an SNR may be freely controlled by detecting all of the detectable signals and adjusting a ratio of a number of values of 0 to a number of values of 1 in a code string used to extract some detected signals from all of the detected signals. Also, since an image is formed using a large number of signals in comparison to a case when only signals emitted at a certain time of every cycle are detected, a high SNR may be ensured.

In another conventional method of eliminating motion blur of a PET image, a deblurring method for restoring a still image by analyzing an image having motion blur and applying the principle of image deconvolution to deblur the image having motion blur has been used. Since all detected signals are used in this conventional method, an SNR is high. However, undesirable noise is generated due to the zero-crossing phenomenon that occurs during the image deconvolution performed to deblur the image having motion blur, and thus image quality is reduced. On the other hand, in the above examples disclosed herein, since the zero-crossing phenomenon does not occur, a relatively clear image may be obtained.

Also, in the examples disclosed herein, a user may freely input a code string used to extract some detected signals from all detected signals enabling an image having a user-desired quality level with respect to a trade-off between an SNR and a motion blur to be generated.

In the examples disclosed herein, sensitivity reduction and noise amplification that occur when a PET image having motion blur is corrected in a conventional method may be eliminated at the same time.

The image processing unit 200, the edge detection unit 211, the motion detection unit 212, the memory 220, the extraction unit 230, the conversion unit 240, the correction unit 250, the PSF estimation unit 251, and the motion blur compensation unit 252 described above may be implemented using one or more hardware components, one or more software components, or a combination of one or more hardware components and one or more software components.

A hardware component may be, for example, a physical device that physically performs one or more operations, but is not limited thereto. Examples of hardware components include amplifiers, differential amplifiers, operational amplifiers, low-pass filters, high-pass filters, band-pass filters, analog-to-digital converters, digital-to-analog converters, registers, differentiators, comparators, arithmetic units, functional units, memory devices, radio cards, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An image correction method comprising:
   detecting signals emitted from a tracer introduced into a target;
   matching the detected signals to codes in a code string in a one-to-one correspondence;
   extracting detected signals of time periods corresponding to the first codes in the code string from the detected signals;
   generating an image of the target using the extracted signals; and
   correcting the generated image based on at least one characteristic of the generated image
   wherein the code string comprises first codes representing time periods for extracting the detected signals and second codes representing time periods for not extracting the detected signals arranged in a sequence in the code string.

2. The image correction method of claim 1, wherein the generated image is a positron emission tomography (PET) image;
   the image correction method further comprises:
      obtaining at least one auxiliary image of the target in addition to the PET image; and
      determining a motion direction of the target as a characteristic of the PET image using the at least one auxiliary image; and
   the correcting comprises correcting the PET image based on the determined motion direction.

3. The image correction method of claim 1, wherein the code string comprises first codes and second codes irregularly arranged in the sequence in the code string.

4. The image correction method of claim 1, wherein the code string comprises first codes and second codes arranged in the sequence in the code string according to an input of a user.

5. The image correction method of claim 1, wherein the code string comprises first codes and second codes arranged in the sequence in the code string; and
   a ratio of a number of the first codes in the code string to a number of the second codes in the code string is equal to or greater than a predetermined reference value.

6. The image correction method of claim 1, wherein the correcting comprises:
   estimating a first filter representing motion blur of the generated image;
   generating a second filter that is an inverse filter of the first filter using the first filter; and
   compensating for the motion blur of the generated image using the second filter.

7. The image correction method of claim 6, wherein the compensating comprises compensating for the motion blur of the generated image by convolving the second filter with the generated image.

8. The image correction method of claim 6, wherein the generating of a second filter comprises converting the first filter into a frequency domain as part of generating the second filter; and all values obtained by converting the first filter into the frequency domain are equal to or greater than a predetermined minimum value.

9. The image correction method of claim 6, wherein the generating of a second filter comprises converting the first filter into a frequency domain as part of generating the second filter; and a difference between a largest value and a smallest value of values obtained by converting the first filter into the frequency domain is equal to or less than a predetermined reference value.

10. A nontransitory computer-readable storage medium storing a computer program for controlling a computer to perform the image correction method of claim 1.

11. An image correction apparatus comprising:

a detection unit configured to detect signals emitted from a tracer introduced into a target;

an extraction unit configured to match the detected signals to the codes in the code string in a one-to-one correspondence and extract detected signals of time periods corresponding to the first codes in the code string from the detected signals;

a conversion unit configured to generate an image of the target using the extracted signals; and a correction unit configured to correct the generated image based on at least one characteristic of the generated image wherein the code string comprises first codes representing time periods for extracting the detected signals and second codes representing time periods for not extracting the detected signals arranged in a sequence in the code string.

12. The image correction apparatus of claim 11, wherein the generated image is a positron emission tomography (PET) image;

the image correction apparatus further comprises:

an auxiliary detection unit configured to obtain at least one auxiliary image of the target in addition to the PET image; and an image analysis unit configured to determine a motion direction of the target as a characteristic of the PET image using the at least one auxiliary image; and the correction unit is further configured to correct the PET image based on the determined motion direction.

13. The image correction apparatus of claim 11, wherein the code string comprises first codes and second codes irregularly arranged in the sequence in the code string.

14. The image correction apparatus of claim 11, wherein the code comprises first codes and second codes arranged in the sequence in the code string; and a ratio of a number of the first codes in the code string to a number of the second codes in the code string is equal to or greater than a predetermined reference value.

15. The image correction apparatus of claim 11, wherein the correction unit comprises:

an estimation unit configured to estimate a first filter representing motion blur of the generated image; and a compensation unit configured to generate a second filter that is an inverse filter of the first filter using the first filter, and compensate for the motion blur of the generated image using the second filter.

16. The image correction apparatus of claim 15, wherein the compensation unit is further configured to compensate for the motion blur of the image by convolving the second filter with the generated image.

17. The image correction apparatus of claim 15, wherein the compensation unit is further configured to convert the first filter into a frequency domain as part of generating the second filter; and all values obtained by converting the first filter into the frequency domain are equal to or greater than a predetermined minimum value.

18. The image correction apparatus of claim 15, wherein the compensation unit is further configured to convert the first filter into a frequency domain as part of generating the second filter; and a difference between a largest value and a smallest value of values obtained by converting the first filter into the frequency domain is equal to or less than a predetermined reference value.

* * * * *